United States Patent
Izawa

(10) Patent No.: US 9,871,904 B2
(45) Date of Patent: Jan. 16, 2018

(54) INFORMATION TRANSMISSION DEVICE AND INFORMATION TRANSMISSION METHOD

(71) Applicant: KYOCERA CORPORATION, Kyoto (JP)

(72) Inventor: Masaki Izawa, Osaka (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/158,239

(22) Filed: May 18, 2016

(65) Prior Publication Data

US 2016/0269528 A1    Sep. 15, 2016

Related U.S. Application Data

(63) Continuation of application No. PCT/JP2014/080774, filed on Nov. 20, 2014.

(30) Foreign Application Priority Data

Nov. 21, 2013  (JP) ................................. 2013-241379

(51) Int. Cl.
*H04M 1/725*     (2006.01)
*G09B 21/00*     (2006.01)
(Continued)

(52) U.S. Cl.
CPC ........ *H04M 1/72519* (2013.01); *G06F 3/016* (2013.01); *G06F 3/03547* (2013.01);
(Continued)

(58) Field of Classification Search
CPC .......... H04M 1/72519; H04M 2250/22; G09B 21/004; G06F 3/03547; G06F 3/041;
(Continued)

(56) References Cited

U.S. PATENT DOCUMENTS 3,932,869 A  *  1/1976  Kane .......................... A61F 9/08
                                                        340/407.2
5,719,561 A  *  2/1998  Gonzales ............. G09B 21/003
                                                        340/4.12
(Continued)

FOREIGN PATENT DOCUMENTS

CN          103268720 A  *  8/2013
JP          2000-059474 A    2/2000
(Continued)

OTHER PUBLICATIONS

Braille Line Using Electrical Stimulation by Puertas et al., dated 2007.*

(Continued)

*Primary Examiner* — Daniel Lai
(74) *Attorney, Agent, or Firm* — Duane Morris LLP

(57) ABSTRACT

An information transmission device includes an information transmission unit configured to tactilely transmit text information, and at least one processor configured to control the information transmission unit. The information transmission unit includes a plurality of stimulation applying units configured to apply tactile stimulation to a touched part of a human body. The at least one processor is configured to control the information transmission unit such that stimulation applying units selected for forming a letter from among the plurality of stimulation applying units produce the tactile stimulation and the tactile stimulation produced by each of the selected stimulation applying units varies in a predetermined order.

8 Claims, 15 Drawing Sheets

(51) Int. Cl.
*G06F 3/01* (2006.01)
*G08B 6/00* (2006.01)
*G06F 3/041* (2006.01)
*H04L 12/58* (2006.01)
*G06F 3/0354* (2013.01)
*A61F 9/08* (2006.01)

(52) U.S. Cl.
CPC .............. *G06F 3/041* (2013.01); *G08B 6/00* (2013.01); *G09B 21/004* (2013.01); *H04L 51/24* (2013.01); *A61F 9/08* (2013.01); *G06F 2203/014* (2013.01); *H04M 2250/22* (2013.01)

(58) Field of Classification Search
CPC ... G06F 3/016; G06F 2203/014; H04L 51/24; G08B 6/00; A61F 9/08
See application file for complete search history.

(56) References Cited

U.S. PATENT DOCUMENTS

| | | | | |
|---|---|---|---|---|
| 6,169,911 | B1* | 1/2001 | Wagner | H04M 1/72522 379/88.14 |
| 9,454,229 | B1* | 9/2016 | Wellen | G06F 3/0416 |
| 2002/0003469 | A1* | 1/2002 | Gupta | G09B 21/005 340/407.1 |
| 2004/0082317 | A1* | 4/2004 | Graefen | H04M 1/6505 455/413 |
| 2004/0239617 | A1* | 12/2004 | Hardwick | G06F 3/016 345/156 |
| 2007/0133770 | A1* | 6/2007 | LaPierre | H04M 1/575 379/142.01 |
| 2012/0173973 | A1* | 7/2012 | Miyauchi | G06F 3/016 715/702 |
| 2012/0293311 | A1* | 11/2012 | Pasquero | G09G 5/00 340/407.1 |
| 2013/0073954 | A1* | 3/2013 | Nieves | G06F 3/016 715/702 |

FOREIGN PATENT DOCUMENTS

| | | |
|---|---|---|
| JP | A 2000-056674 | 2/2000 |
| JP | 2006-163206 A | 6/2006 |
| JP | 2009-032139 A | 2/2009 |
| JP | 2011-002926 A | 1/2011 |

OTHER PUBLICATIONS

International Search Report in International Application No. PCT/JP2014/080774, dated Feb. 3, 2015.
Written Opinion of the International Searching Authority in International Application No. PCT/JP2014/080774, dated Feb. 3, 2015, with Statement of Relevance of Non-English References, in 5 pages.

* cited by examiner

FIG.4

| LETTER | CONTROL DATA |
|---|---|
| LETTER 1 | DATA 1 |
| LETTER 2 | DATA 2 |
| LETTER 3 | DATA 2 |
| LETTER 4 | DATA 4 |
| LETTER 5 | DATA 5 |
| ⋮ | ⋮ |

12a

ENERGIZING PATTERN TABLE

HOME SCREEN

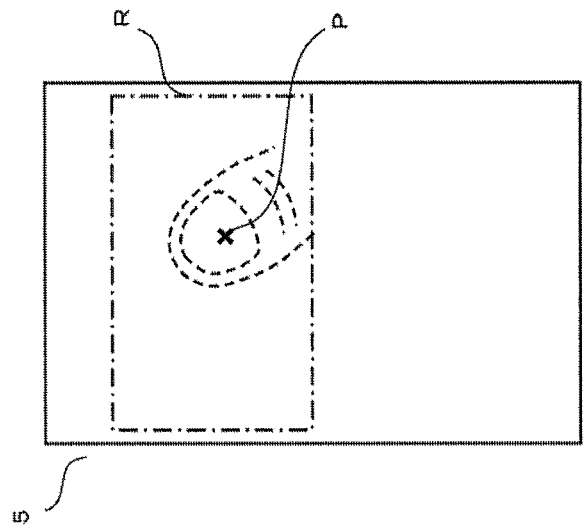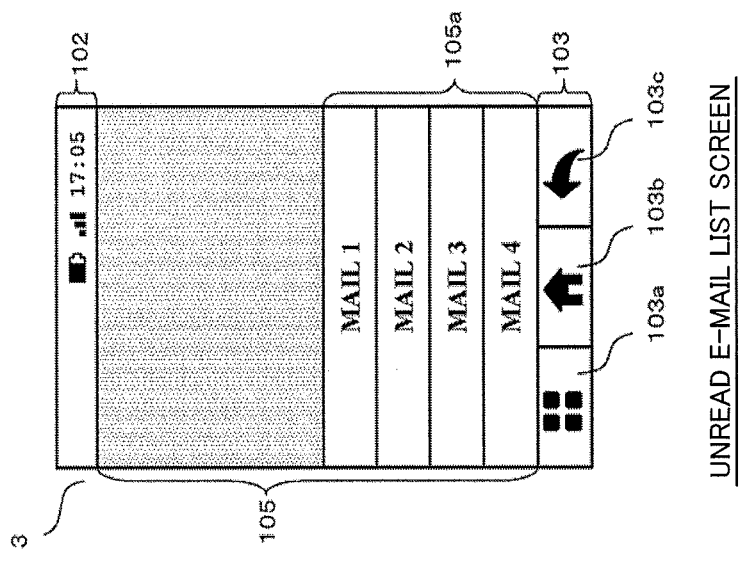

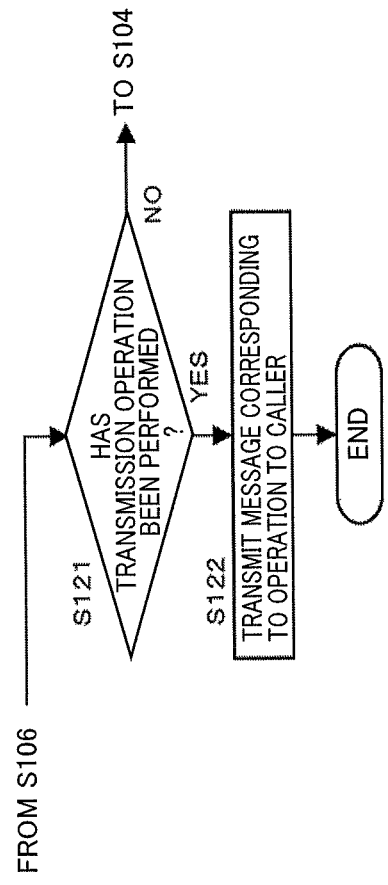

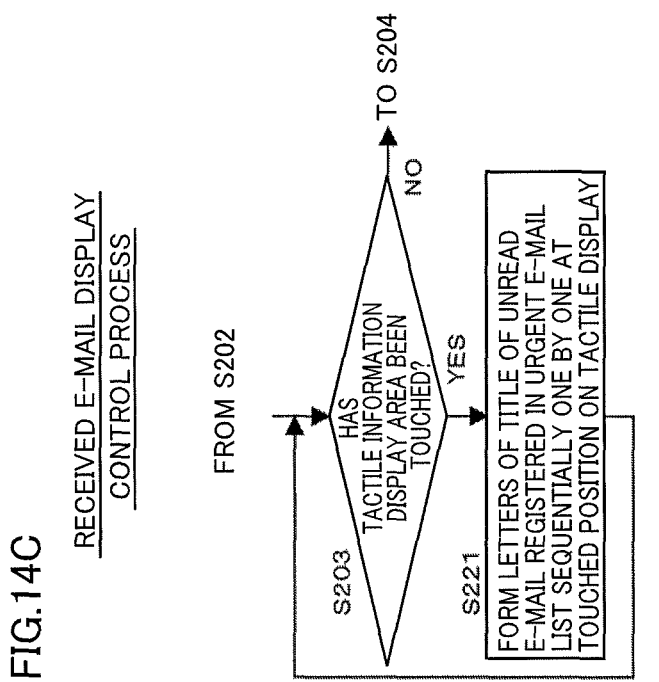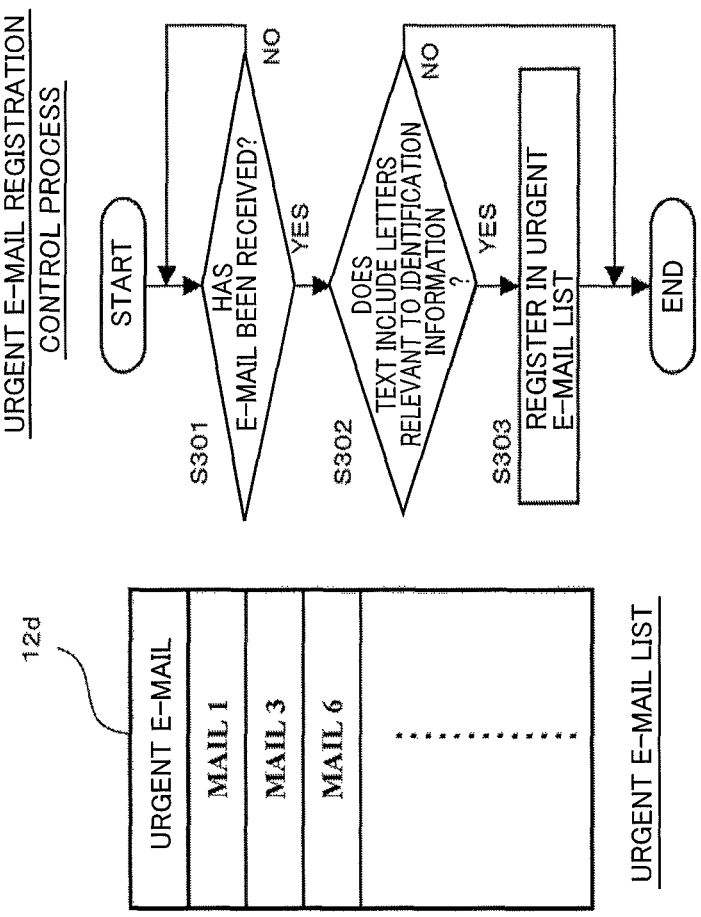

INFORMATION TRANSMISSION DEVICE AND INFORMATION TRANSMISSION METHOD

CROSS-REFERENCE TO RELATED APPLICATION

The present application is a continuation based on PCT Application No. PCT/JP2014/080774 filed on Nov. 20, 2014, which claims the benefit of Japanese Application No. 2013-241379, filed on Nov. 21, 2013. PCT Application No. PCT/JP2014/080774 is entitled "Information Transmission Device and Information Transmission Method", and Japanese Application No. 2013-241379 is entitled "Information Transmission Device, Information Transmission Method and Program." The content of which are incorporated by reference herein in their entirety.

FIELD

The present disclosure relates to an information transmission device which transmits various types of information to a user, such as a mobile phone, a PDA (Personal Digital Assistant), a tablet PC, and a personal computer. The present disclosure relates to an information transmission method applicable to such an information transmission device.

BACKGROUND

A mobile phone conventionally transmits various types of information to a user by means of a display on a display or sound from a speaker. Such visual or acoustic information transmission may be undesirable.

For example, if one receives e-mail during a meeting, he/she would hesitate to stare at the display in order to check information on the e-mail during the meeting. Of course, information on the e-mail cannot be transmitted to a user by sound during the meeting.

SUMMARY

An aspect relates to an information transmission device. The information transmission device of the aspect includes an information transmission unit configured to tactilely transmit text information, and at least one processor configured to control the information transmission unit. The information transmission unit includes a plurality of stimulation applying units configured to apply tactile stimulation to a touched part of a human body. The at least one processor is configured to control the information transmission unit such that stimulation applying units selected for forming a letter from among the plurality of stimulation applying units produce the tactile stimulation and the tactile stimulation produced by each of the selected stimulation applying units varies in a predetermined order.

BRIEF DESCRIPTION OF THE DRAWINGS

FIG. 4 shows a structure of an energizing pattern table according to an embodiment.

FIG. 10A shows an image display according to an embodiment with an unread e-mail list screen displayed thereon.

FIG. 10B shows the tactile display with the tactile information display area set thereon.

FIG. 13A shows a structure of a message list according to Variation 1.

FIG. 13B is a flowchart showing a phone call control process according to Variation 1.

FIG. 14A represents an urgent e-mail list according to Variation 2.

FIG. 14B is a flowchart showing an urgent e-mail registration control process according to Variation 2.

FIG. 14C is a flowchart showing a received e-mail display control process according to Variation 2.

DETAILED DESCRIPTION

When visual or acoustic information transmission is difficult, it is conceivable to transmit information tactilely. A tactile display is one of means for tactilely transmitting information. For instance, as an example of a tactile display, a configuration may be adopted in which a plurality of electrodes are located in a matrix on a substrate and electrodes corresponding to the shape of a letter are vibrated, thereby transmitting the shape of the letter to a user's finger or the like touching the vibrating electrodes.

With the tactile display of the above configuration, respective electrodes forming a letter give uniform tactile stimulation to a finger or the like. When the letter is not simple like a Braille letter, it may be difficult for a user to perceive the shape of the letter with his/her finger or the like without receiving some degree of training. According to an embodiment of the present disclosure, the user can perceive the shape of the letter with his/her finger or the like without receiving such training.

Hereinafter, an embodiment will be described with reference to the drawings.

Figure 1:
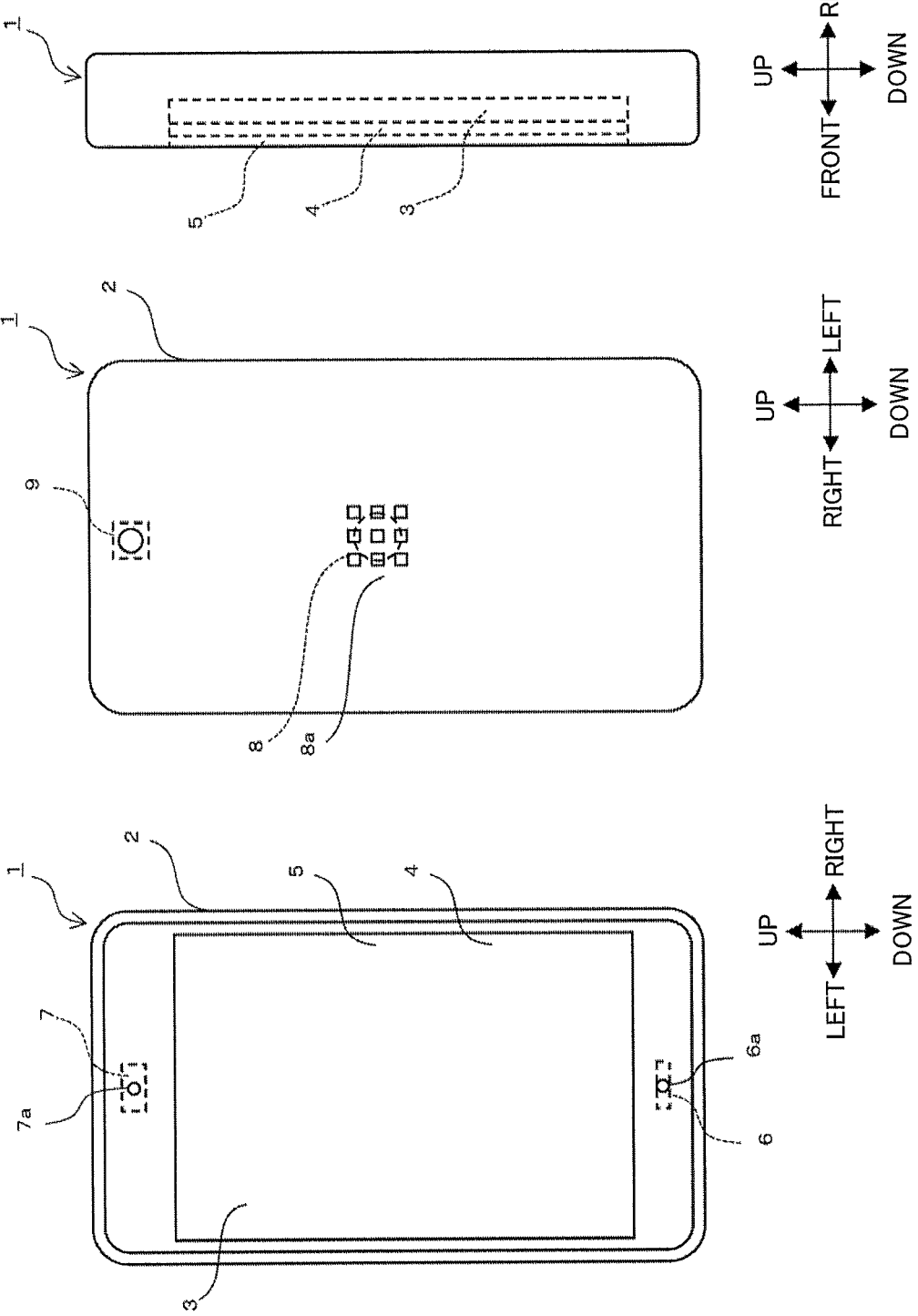
FIG. 1A is a front view showing a configuration of a mobile phone according to an embodiment.
FIG. 1B is a rear view showing the configuration of the mobile phone according to an embodiment.
FIG. 1C is a right side view showing the configuration of the mobile phone according to an embodiment.

FIGS. 1A to 1C show a front view, a rear view and a right side view of a mobile phone 1, respectively. Hereinafter, as shown in FIGS. 1A to 1C, the longer direction of a cabinet 2 is defined as the up/down direction, and the shorter direction of cabinet 2 is defined as the left/right direction, for ease of description. The direction perpendicular to these up/down and left/right directions is defined as the front/rear direction.

As shown in FIGS. 1A to 1C, mobile phone 1 includes cabinet 2, image display 3, a touch panel 4, a tactile display 5, a microphone 6, a conversation speaker 7, an external speaker 8, and a camera 9.

Cabinet 2 can have a substantially rectangular profile as seen from the front surface. Image display 3 can be located on the front surface side of cabinet 2. Various types of images (screens) can be displayed on image display 3. Image display 3 may be a liquid crystal display, for example. Image display 3 may be a display of another type, such as an organic electroluminescence display. Touch panel 4 can be located to cover image display 3. Touch panel 4 may be formed as a transparent sheet. As touch panel 4, various types of touch panels, such as capacitance type, ultrasonic type, pressure-sensitive type, resistive film type, and optical sensing type touch panels, may be used.

Tactile display 5 can be located on the front surface of cabinet 2 to cover touch panel 4. Tactile display 5 can display information in the form that can be tactilely transmitted to a user.

Figure 2:
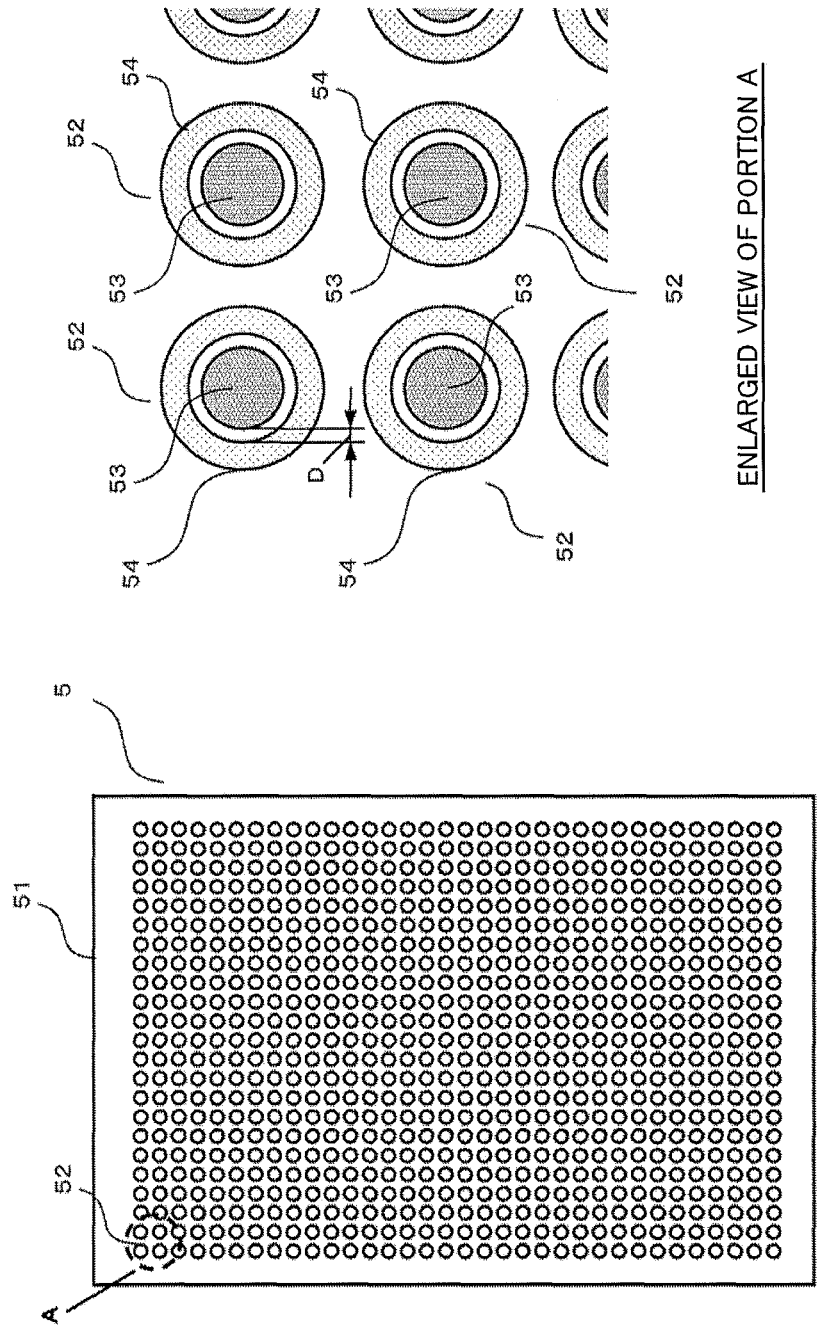
FIG. 2A shows a structure of a tactile display according to an embodiment.
FIG. 2B is an enlarged view of a portion A in FIG. 2A, showing a structure of electrode units.

FIG. 2A shows a structure of tactile display 5. FIG. 2B is an enlarged view of a portion A in FIG. 2A, showing a structure of electrode units 52.

Tactile display 5 can have a shape and a size substantially identical to those of image display 3 and touch panel 4. Tactile display 5 can include a transparent substrate 51 and a plurality of transparent electrode units 52 located in a matrix almost entirely on substrate 51. Each electrode unit 52 can include a stimulating electrode 53 having a circular shape and an annular indifferent electrode 54 located to surround stimulating electrode 53. A predetermined interval D can be left between stimulating electrode 53 and indifferent electrode 54 such that they are insulated from each other.

Both touch panel 4 and tactile display 5 overlaid on image display 3 may be transparent. A user can see an image (screen) displayed on image display 3 through these touch panel 4 and tactile display 5.

Returning to FIGS. 1A to 1C, microphone 6 can be located at the lower end within cabinet 2. Conversation speaker 7 can be located at the upper end within cabinet 2. Microphone 6 can receive voice passed through a microphone hole 6a located in the front surface of cabinet 2. Microphone 6 can generate an electrical signal in accordance with received sound. Conversation speaker 7 can output sound. The output sound can be emitted out of cabinet 2 through an output hole 7a located in the front surface of cabinet 2. At the time of a call, received voice from a device of a communication partner (mobile phone etc.) can be output through conversation speaker 7. User's uttered voice can be input to microphone 6. The sound can include various types of sound, such as voice and an audible alert.

External speaker 8 can be located within cabinet 2. An output hole 8a can be located in the rear surface of cabinet 2 in a region facing external speaker 8. Sound output through external speaker 8 can be emitted out of cabinet 2 through output hole 8a.

At the upper part of cabinet 2, a camera 9 can be located on the rear surface side. Camera 9 can include an imaging device, such as a CCD (Charge Coupled Device) or a CMOS sensor (Complementary Metal Oxide Semiconductor), and can capture an image of a subject.

Figure 3:
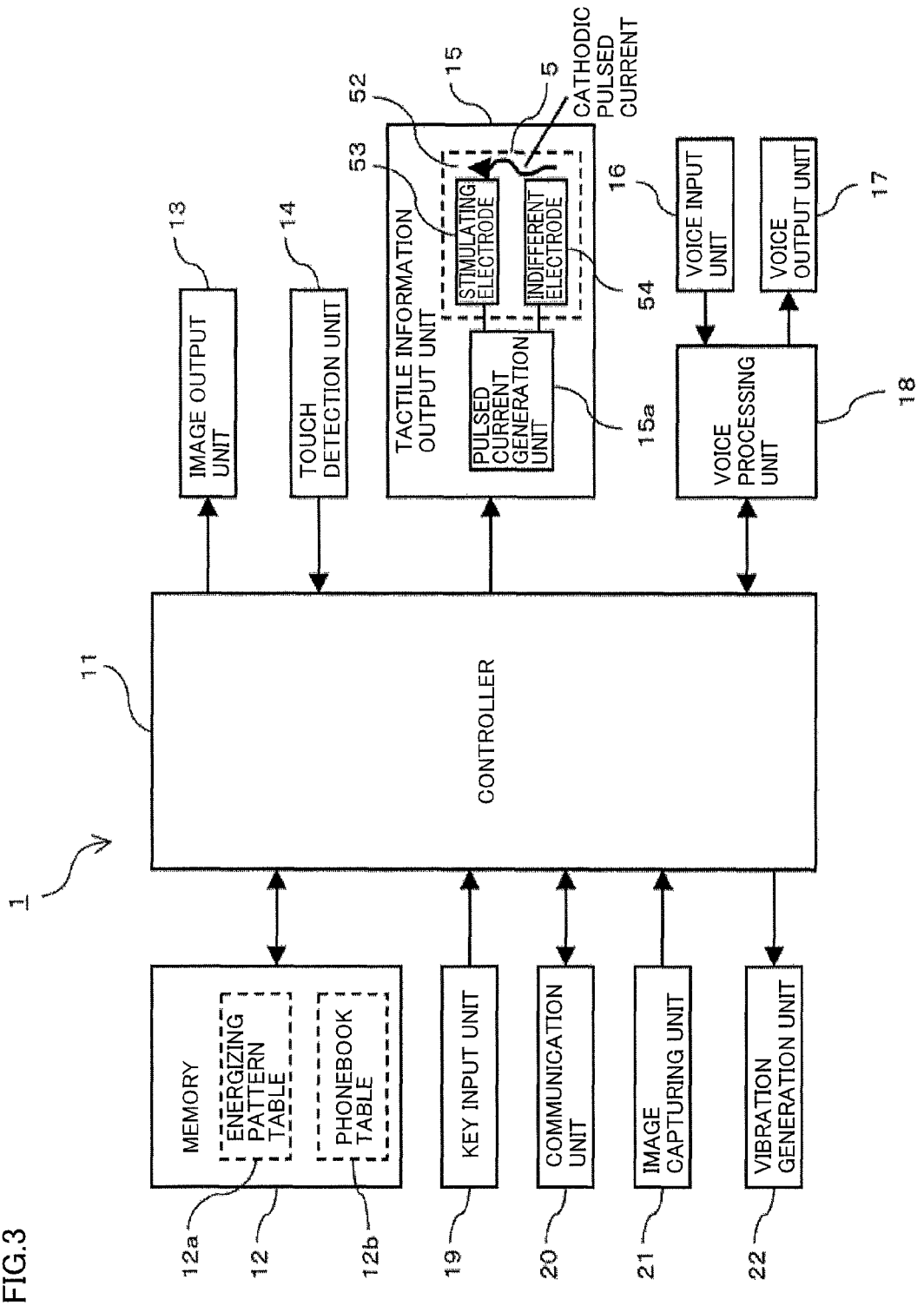
FIG. 3 is a block diagram showing an overall configuration of the mobile phone according to an embodiment.

FIG. 3 is a block diagram showing an overall configuration of mobile phone 1.

As shown in FIG. 3, mobile phone 1 includes a controller 11, a memory 12, an image output unit 13, a touch detection unit 14, a tactile information output unit 15, a voice input unit 16, a voice output unit 17, a voice processing unit 18, a key input unit 19, a communication unit 20, an image capturing unit 21, and a vibration generation unit 22.

Memory 12 may include at least one of a ROM (Read Only Memory), a RAM (Random Access Memory), and an external memory. Memory 12 can have various types of programs stored therein. The programs stored in memory 12 include various application programs (hereinafter briefly referred to as "applications"), for example, applications for telephone, message, camera, web browser, map, game, schedule management, and the like, in addition to a control program for controlling each unit of mobile phone 1. The programs stored in memory 12 may also include programs for executing a phone call control process and a received e-mail display control process which will be described later. The programs are stored in memory 12 by a manufacturer during manufacture of mobile phone 1, or may be stored in memory 12 through a communication network or storage medium, such as a memory card or CD-ROM.

Memory 12 can also include a working area for storing data temporarily utilized or generated while a program is executed.

Memory 12 can have an energizing pattern table 12a stored therein for use in controlling tactile information output unit 15. FIG. 4 shows a structure of energizing pattern table 12a. Energizing pattern table 12a can store various types of letters (including numbers and symbols) and control data for forming the letters on tactile display 5 in association with each other. The control data can include layout information of each electrode unit 52 to be energized to form each letter and information on the order of varying the frequency of a pulsed current to be flown into each electrode unit 52.

Memory 12 can have a phonebook table 12b stored therein. Phonebook table 12b can have contact information on communication partners registered therein. The contact information can be composed of contact information on each communication partner, including the name, telephone number, e-mail address, address, belonging group and the like.

Controller 11 includes at least one processor. The processor includes one or more circuits or units configurable to perform one or more data computing procedures or processes. In accordance with various embodiments, the at least one processor may be implemented as a single integrated circuit (IC) or as multiple communicatively coupled IC's and/or discrete circuit. The at least one processor includes CPU (Central Processing Unit), for example. In accordance with a program stored in memory 12, the at least one processor can control each unit constituting mobile phone 1 (memory 12, image output unit 13, touch detection unit 14, tactile information output unit 15, voice input unit 16, voice output unit 17, voice processing unit 18, key input unit 19, communication unit 20, image capturing unit 21, vibration generation unit 22, and the like). The following processing by controller 11 is executed by the at least one processor.

Image output unit 13 may include image display 3 shown in FIG. 1A. Image output unit 13 can cause image display 3 to display an image (screen) based on a control signal and an image signal received from controller 11. Image output unit 13 can turn on, turn off, and adjust brightness of, image display 3 in response to control signals received from controller 11.

Touch detection unit 14 can include touch panel 4 shown in FIG. 1A, and can detect a touch operation on touch panel 4. More specifically, touch detection unit 14 can detect a position (hereinafter referred to as a "touch position") at which a contact object, such as a user's finger, contacts touch panel 4. Touch detection unit 14 can output a position signal generated based on a detected touch position to controller 11. The touch operation on touch panel 4 is performed on a screen or an object displayed on image display 3, and can be rephrased as a touch operation on image display 3.

Touch detection unit 14 may be configured to, when a user's finger has approached display 3 (touch panel 4), detect a position where the user's finger has approached as a touch position. For example, when touch panel 4 of touch detection unit 14 is of a capacitance type, the sensitivity thereof can be adjusted such that a change in capacitance exceeds a detection threshold value when a finger has approached touch panel 4.

When touch panel 4 is covered with tactile display 5 as in an embodiment, a finger is not brought into direct contact with touch panel 4, but into indirect contact with touch panel 4 through tactile display 5 interposed therebetween. Touch panel 4 can detect a touch position when a finger contacts or approaches tactile display 5.

A user can perform various touch operations on image display 3 by touching touch panel 4 with his/her finger or bringing his/her finger closer thereto. The touch operation includes a tap operation, a flick operation, a sliding operation, a double-tap operation, and the like, for example. The tap operation is an operation that a user contacts touch panel 4 with his/her finger or brings his/her finger closer thereto, and then lifts the finger from touch panel 4 after a short time period. The flick operation is an operation that a user contacts touch panel 4 with his/her finger or brings his/her finger closer thereto, and then flicks or sweeps touch panel 4 with the finger in any direction. The sliding operation is an operation that a user moves his/her finger in any direction with the finger kept in contact with or in proximate to touch panel 4. The double-tap operation is an operation of repeating a tap operation twice in a short time period.

For example, in the case where touch detection unit 14 detects a touch position, when the touch position is no longer detected within a predetermined first time period after the touch position is detected, controller 11 can determine that the touch operation is a tap operation. In the case where a touch position is moved by a predetermined first distance or more within a predetermined second time period after the touch position is detected, and then the touch position is no longer detected, controller 11 can determine that the touch operation is a flick operation. When a touch position is moved by a predetermined second distance or more after the touch position is detected, controller 11 can determine that the touch operation is a sliding operation. When a tap operation is detected twice within an interval of a predetermined third time period, controller 11 can determine that the touch operation is a double-tap operation.

Tactile information output unit 15 includes tactile display 5 shown in FIG. 1A and a pulsed current generation unit 15a. Pulsed current generation unit 15a can apply a pulsed voltage for flowing a cathodic pulsed current across stimulating electrode 53 and indifferent electrode 54 based on a control signal from controller 11. If the pulsed voltage is applied with a finger touching electrode unit 52, the cathodic pulsed current flows into the finger.

Voice input unit 16 may include microphone 6. Voice input unit 16 can output an electrical signal from microphone 6 to voice processing unit 18.

Voice output unit 17 may include conversation speaker 7 and external speaker 8 shown in FIG. 1A. An electrical signal received from voice processing unit 18 can be input to voice output unit 17. Voice output unit 17 can cause sound to be output through conversation speaker 7 or external speaker 8.

Voice processing unit 18 can perform A/D conversion or the like on an electrical signal received from voice input unit 16, and can output a digital audio signal after conversion to controller 11. Voice processing unit 18 can perform decoding and D/A conversion or the like on a digital audio signal received from controller 11, and can output an electrical signal after conversion to voice output unit 17.

Key input unit 19 includes at least one or more hard keys. For example, key input unit 19 includes a power key for turning on mobile phone 1, and the like. Key input unit 19 can output a signal corresponding to a pressed hard key to controller 11.

Communication unit 20 includes a circuit for converting a signal, an antenna that transmits/receives electric waves, and the like, in order to make calls and communications. Communication unit 20 can convert a signal for a call or communication received from controller 11 into a radio signal, and can transmit the converted radio signal to a communication destination, such as a base station or another communication device, through the antenna. Communication unit 20 can convert a radio signal received through the antenna into a signal in the form that can be utilized by controller 11, and can output the converted signal to controller 11.

Image capturing unit 21 includes camera 9 shown in FIG. 1B. Image capturing unit 21 can perform various types of image processing on image data of an image captured by camera 9, and can output the image data after image processing to controller 11.

Vibration generation unit 22 includes a vibrator and a driving unit for the vibrator, and can transmit vibrations of the vibrator to cabinet 2 to vibrate cabinet 2.

In mobile phone 1, various screens can be displayed on image display 3, and a user can make various touch operations on the screens. For example, as an initial screen, a home screen 101 can be displayed on image display 3.

Figure 5:
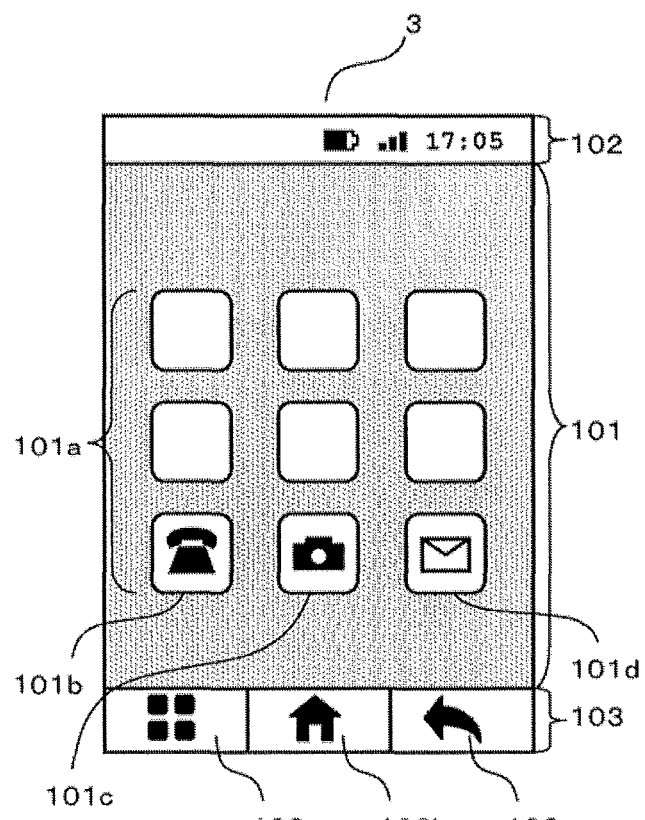
FIG. 5 shows an image display with a home screen displayed thereon according to an embodiment.

FIG. 5 shows image display 3 with home screen 101 displayed thereon. Home screen 101 can include start-up icons 101a for starting up various types of applications. Start-up icons 101a can include a telephone icon 101b, a camera icon 101c, an e-mail icon 101d, and the like, for example.

Home screen 101, a notification bar 102 and an operation key group 103 can be displayed on image display 3. Notification bar 102 can be displayed above home screen 101 displayed on image display 3. Notification bar 102 can include a current time, a capacity meter indicating the battery capacity, a strength meter indicating the strength of electric waves, and the like. Operation key group 103 can be displayed under home screen 101. Operation key group 103 can be composed of a setting key 103a, a home key 103b and a back key 103c. Setting key 103a is a key mainly for causing image display 3 to display a setting screen for performing various types of setting. Home key 103b is a key mainly for causing the display of image display 3 to shift to home screen 101 from another screen. Back key 103c is a key mainly for returning executed processing to processing of an immediately preceding step.

When utilizing various applications, a user can perform a tap operation on start-up icon 101a corresponding to an application to be utilized. The application can be started up, and an execution screen based on the application can be displayed. Notification bar 102 and operation key group 103 can be continuously displayed on image display 3 even when the execution screen of the started-up application is displayed or the execution screen transitions with the progress of the application.

Mobile phone 1 can visually transmit text information, image information or the like to a user by displaying an image on image display 3, as shown in FIG. 5. In an embodiment, mobile phone 1 can transmit text information to a user not only visually but also tactilely as it includes tactile information output unit 15 including tactile display 5. Controller 11 can control tactile information output unit 15.

Figure 6B:
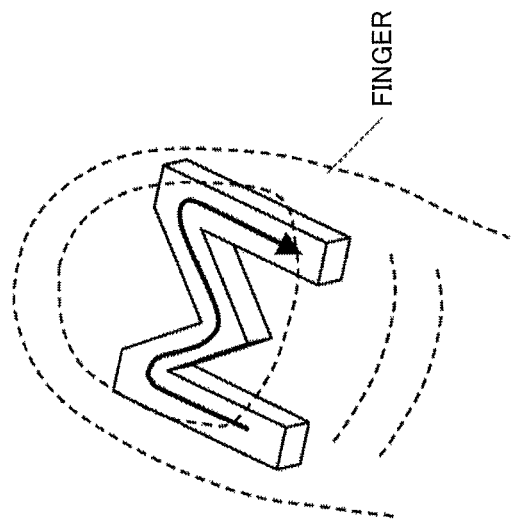
FIGS. 6A to 6C are explanatory drawings of a control operation for transmitting text information to a user performed by a controller according to an embodiment.
Figure 6A:
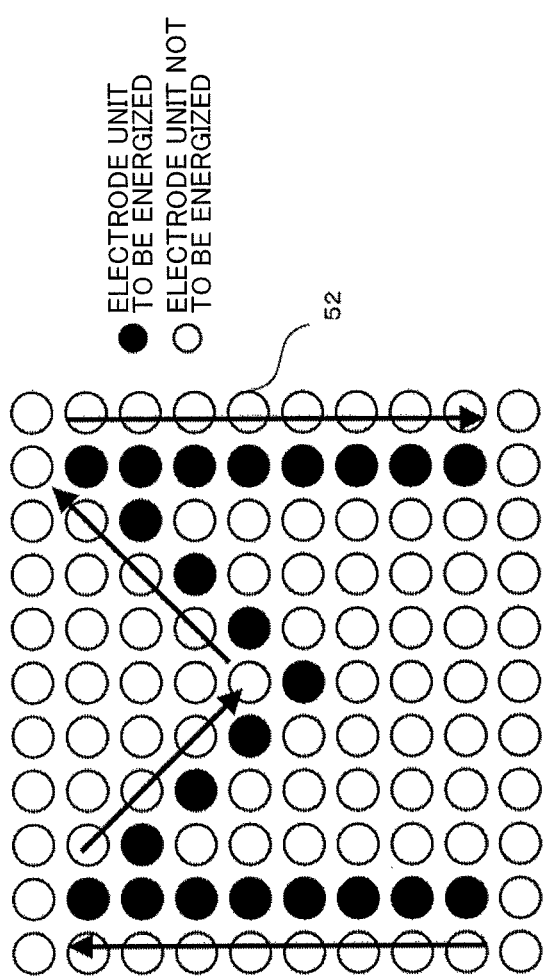
Figure 6C:
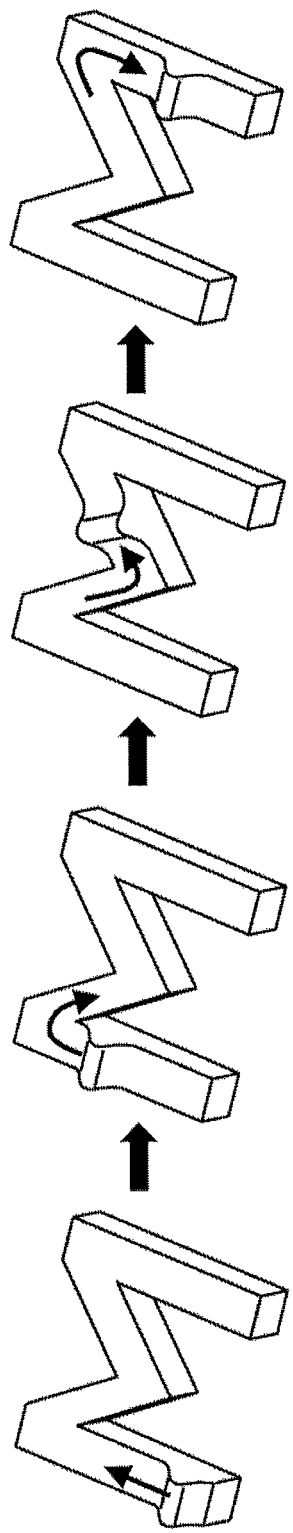

FIGS. 6A to 6C are explanatory drawings of a control operation for transmitting text information to a user performed by controller 11. FIGS. 6A to 6C show an instance where the alphabet letter "M" is transmitted to a user.

When transmitting a predetermined letter to a user by tactile display 5, controller 11 can perform a protrusion control operation of supplying a finger with a touch as if the finger touches a letter uniformly protruding from the surface of tactile display 5 and, subsequent to the protrusion control operation, can perform a trace control operation of supplying the finger with a touch as if the shape of a letter is traced with the finger.

First, the protrusion control operation will be described. Controller 11 can select electrode units 52 for forming a letter to be transmitted with reference to energizing pattern table 12a. Controller 11 can output a control signal to pulsed current generation unit 15a, and as shown in FIG. 6A, can apply a pulsed voltage for flowing a cathodic pulsed current of a predetermined frequency into selected electrode units 52.

A cutaneous sensation perceived at the skin surface of a finger is received by a tactile receptor. The tactile receptor that detects a mechanical deformation and a contact pressure is called a mechanical receptor. When a finger is touching selected electrode unit 52, the cathodic pulsed current of a predetermined frequency flows into the finger. This cathodic pulsed current applies electrical stimulation which is tactile stimulation to the finger touching electrode unit 52. This electrical stimulation fires the Merkel's disk which is one of mechanical receptors. The Merkel's disk has detected a displacement of the skin, i.e., a pressure, and when the electrical stimulation fires the Merkel's disk, a user will feel a simulated touch as if he/she has touched a projecting feature with his/her finger. If respective electrode units 52 constituting a letter apply electrical stimulation to a finger uniformly, a user will feel a touch as if he/she is touching with his/her finger a letter protruding from the surface of tactile display 5 as shown in FIG. 6B.

Next, the trace control operation will be described. In the Merkel's disk, a detected pressure and a firing frequency have a correlation, and as the pressure increases (the displacement of the skin increases), the firing frequency increases. If the firing frequency of the Merkel's disk increases by increasing the frequency of the pulsed current, a user will feel a touch as if he/she has touched with his/her finger a projecting feature protruding to a higher level.

After the pulsed current is uniformly flown into all of selected electrode units 52, controller 11, with reference to energizing pattern table 12a, can flow a pulsed current of a frequency higher than the previous frequency sequentially into respective selected electrode units 52 in accordance with the order indicated by the control data, as indicated by the arrows in FIG. 6A. Accordingly, as shown in FIG. 6C, a user feels as if an even higher projecting portion is formed on the protruding letter and the projecting portion moves with time. Since controller 11 thus controls tactile information output unit 15 such that electrical stimulation produced by each of selected electrode units 52 varies in a predetermined order, a user feels a touch as if the shape of a letter to be transmitted is traced with the surface of his/her finger as indicated by the arrow in FIG. 6B.

(Operation when Receiving Call)

When there is an incoming call to mobile phone 1, caller information, for example, the telephone number, name and the like can be displayed on image display 3. Usually, a user becomes aware of a caller by looking at the caller information displayed on image display 3. If there is an incoming call in a situation where a user hesitates to look at image display 3, such as during a meeting, the user cannot look at the caller information displayed on image display 3. In an embodiment, when there is an incoming call, controller 11 executes a phone call control process of tactilely transmitting the caller information to a user via tactile display 5.

Figure 7:
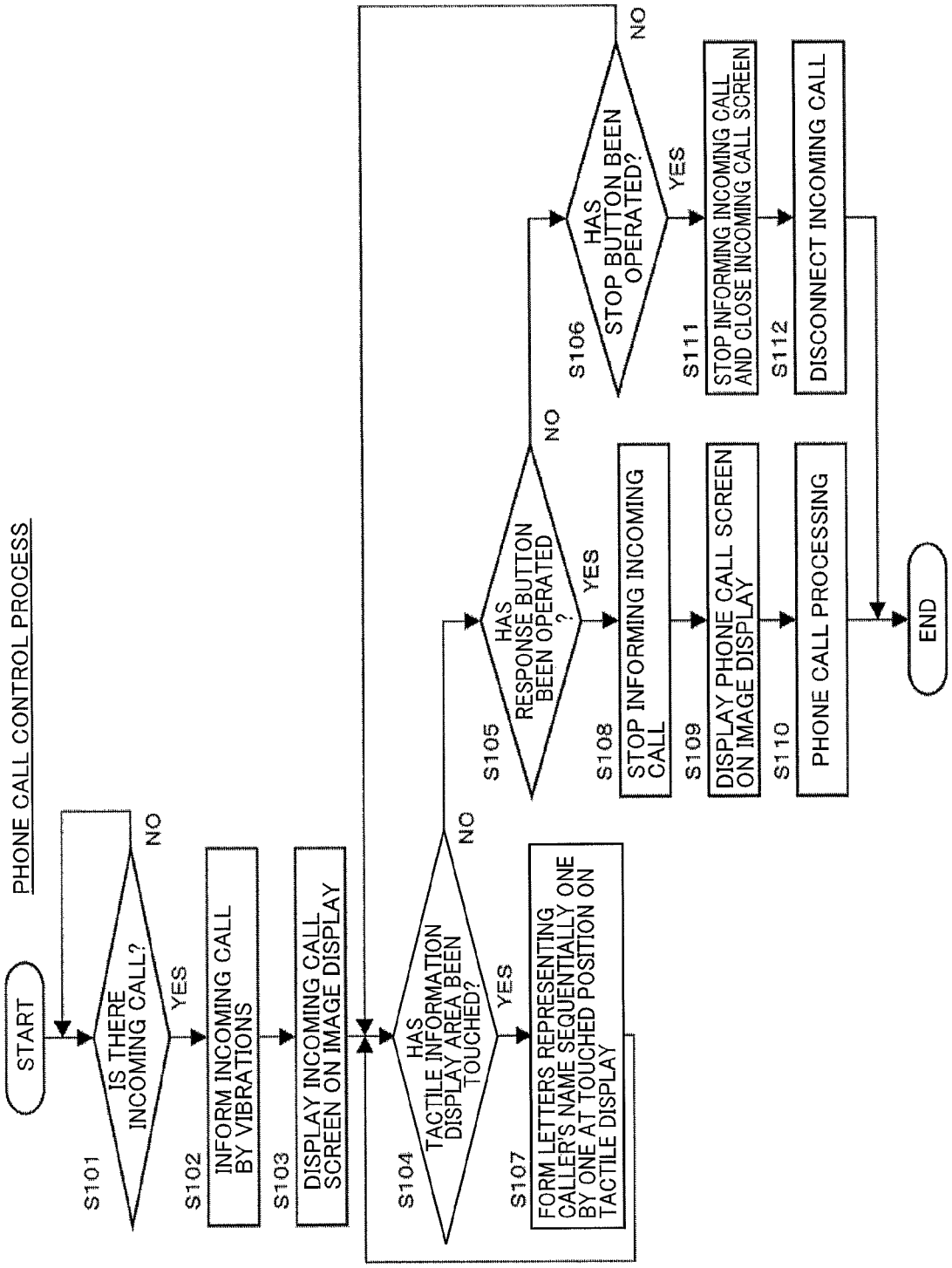
FIG. 7 is an example of a flowchart showing a phone call control process according to an embodiment.
Figure 8A:
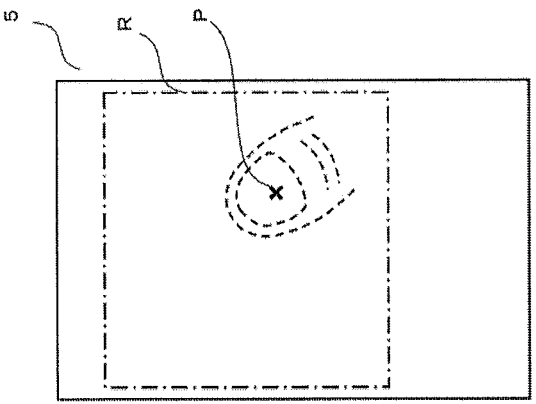
FIG. 8A shows an image display with an incoming call screen displayed thereon according to an embodiment.
Figure 8B:
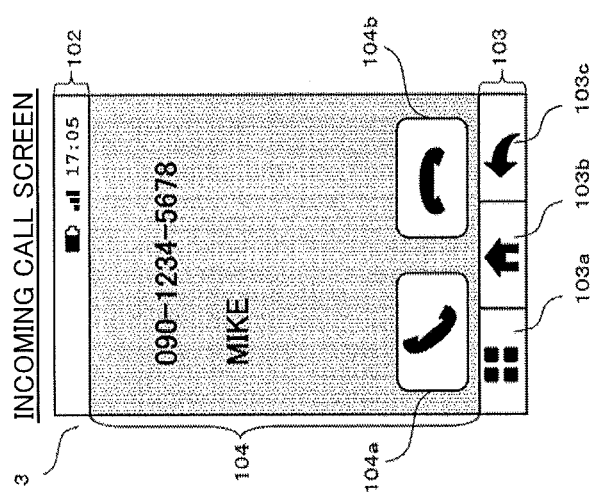
FIG. 8B shows a tactile display with a tactile information display area set thereon.
Figure 8C:
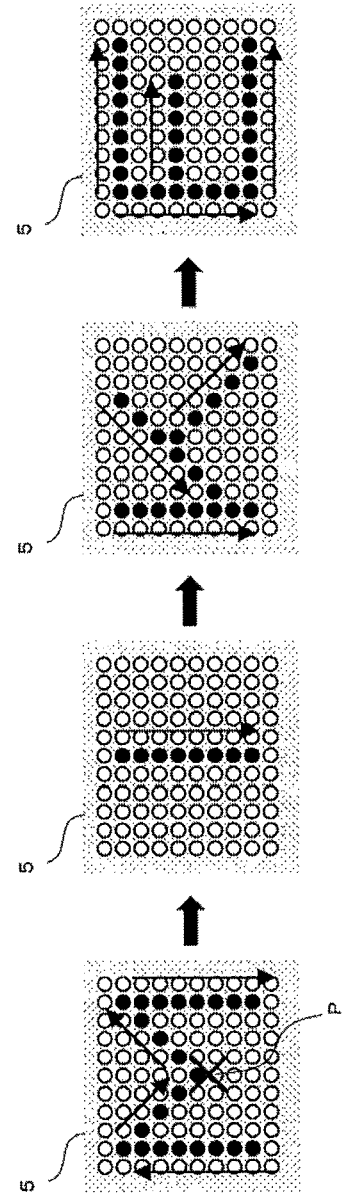
FIG. 8C shows how the caller's name is displayed on the tactile display.

FIG. 7 is an example of a flowchart showing a phone call control process. FIG. 8A shows image display 3 with an incoming call screen 104 displayed thereon. FIG. 8B shows tactile display 5 with a tactile information display area R set thereon. FIG. 8C shows how the caller's name is displayed on tactile display 5. FIGS. 8A to 8C show an instance where a phone call has been received from a caller named "MIKE."

When a user selects a manner mode in which an incoming call is informed by vibrations of vibration generation unit 22, the phone call control process shown in FIG. 7 is executed.

Referring to FIG. 7, when there is an incoming call (YES in S101), controller 11 can activate vibration generation unit 22 to inform an incoming call by vibrations (S102). Controller 11 can control image output unit 13 to cause image display 3 to display incoming call screen 104 (S103). As shown in FIG. 8A, incoming call screen 104 includes the caller's telephone number and name which are the caller information. Incoming call screen 104 includes a response button 104a and a stop button 104b. The caller's name can be extracted from phonebook table 12b based on the telephone number received by communication unit 20.

As shown in FIG. 8B, controller 11 can set tactile information display area R in a region on tactile display 5 avoiding notification bar 102, operation key group 103, response button 104a, and stop button 104b. In order to detect that a touch has been made in tactile information display area R, controller 11 can set a detection area corresponding to tactile information display area R on touch panel 4.

When incoming call screen 104 is displayed, controller 11 can monitor whether or not tactile information display area R has been touched, whether or not response button 104a has been operated, and whether or not stop button 104b has been operated (S104, S105, S106). An operation on response button 104a is a tap operation on response button 104a, for example. An operation on stop button 104b is a tap operation on stop button 104b, for example.

For example, in a situation where a user cannot look at image display 3 but wants to know who is the caller, he/she can touch tactile information display area R with his/her finger, as shown in FIG. 8B. Since tactile information display area R exists relatively widely from the center toward the upper portion of tactile display 5, the user can touch tactile information display area R even by operating mobile phone 1 gropingly. Touch detection unit 14 can detect a touched position P.

When tactile information display area R has been touched (YES in S104), controller 11 can form the letters representing the caller's name at touched position P sequentially one by one (S107), as shown in FIG. 8C. On this occasion, controller 11 can perform the protrusion control operation and the trace control operation described with reference to FIGS. 6A to 6C sequentially on each letter. The arrows shown in FIG. 8C indicate the order in which the letters are traced. A time period during which no letter is formed exists among the letters.

After terminating the operation in step S107, controller 11 can return the process to step S104, and can monitor again whether or not tactile information display area R has been touched. On this occasion, when tactile information display area R continues being touched since the previous display of the name, controller 11 does not determine that a touch has been made, but can determine that a touch has been made once a finger is released from tactile information display area R and touches tactile information display area R again.

A user can operate response button 104a when answering a call. When response button 104a has been operated (YES in S105), controller 11 can stop informing incoming call (S108), and can then cause image display 3 to display a phone call screen (S109) instead of incoming call screen 104 to perform phone call processing (S110). After establishing a communication path with a call partner's telephone (mobile phone), controller 11 can output received voice received by communication unit 20 through conversation speaker 7, and can transmit user's uttered voice input through microphone 6 to the call partner's telephone from communication unit 20. When a call termination button located on the phone call screen is operated, controller 11 can stop the phone call processing. The phone call control process is thereby terminated.

When not answering a call, a user can operate stop button 104b. When stop button 104b has been operated (YES in S106), controller 11 can stop informing the incoming call and close incoming call screen 104 (S111). Controller 11 can then disconnect the incoming call (S112). The phone call control process is thereby terminated.

In the flowchart of FIG. 7, if a user operates stop button 104b (YES in S106), controller 11 shall stop informing the incoming call and close incoming call screen 104 (S111), and shall disconnect the incoming call (S112), but this is not a limitation.

For example, if a user operates stop button 104b, controller 11 may stop informing the incoming call and switch incoming call screen 104 to an answer holding screen to hold the incoming call. If a user operates stop button 104b again while holding the incoming call, controller 11 may disconnect the incoming call.

The flowchart of FIG. 7 represents a process while receiving a call. When a partner's terminal performs disconnection processing before the operations in S104 to S106, the phone call control process of FIG. 7 is terminated.

In order to prevent a user's misoperation more effectively, controller 11 may perform the operation in step S107 if a user performs a sliding operation in tactile information display area R, for example, rather than proceeding to the operation in step S107 when a user touches tactile information display area R. In this case, controller 11 may form the letters representing the caller's name sequentially one by one at a position of the end point of the sliding operation performed by the user (S107).

In order to prevent a user's misoperation more effectively, it may be determined that response button 104a or stop button 104b has been operated when a specific operation, such as a flick operation, for example, that may be less likely to happen accidentally than a tap operation is performed.

In step S104, when it is determined that tactile information display area R has been touched, controller 11 may stop vibrations produced by vibration generation unit 22. When a hard key is pressed aside from a touch operation on touch panel 4 by a user, controller 11 may stop vibrations produced by vibration generation unit 22.

In an embodiment, the phone call control process of FIG. 7 is executed when the manner mode is set, but the phone call control process of FIG. 7 may always be executed as a control process for the telephone function. In this case, if the normal mode has been set, an incoming call is informed by a ring tone in step S102, and if the manner mode has been set, an incoming call is informed by vibrations in step S102. In this case, if it is determined in step S104 that tactile information display area R has been touched, controller 11 may stop a ring tone or vibrations. Instead of or in addition to the caller's name, the caller's telephone number may be displayed on tactile display 5.

(Operation when Receiving E-Mail)

In mobile phone 1, when e-mail is received, information on the received e-mail (title, sender, text, etc.) can be displayed on image display 3 based on a predetermined viewing operation performed by a user. A user can check the information on the e-mail displayed on image display 3. During a meeting, however, it is difficult for a user to make the information on e-mail displayed on image display 3 and to look at the information. In such a case, it is preferable that the user can check at least part of the information on the e-mail in a manner that does not attract great public attention. In an embodiment, controller 11 can execute a received e-mail display control process of tactually transmitting information on unread e-mail to a user via tactile display 5.

Figure 9:
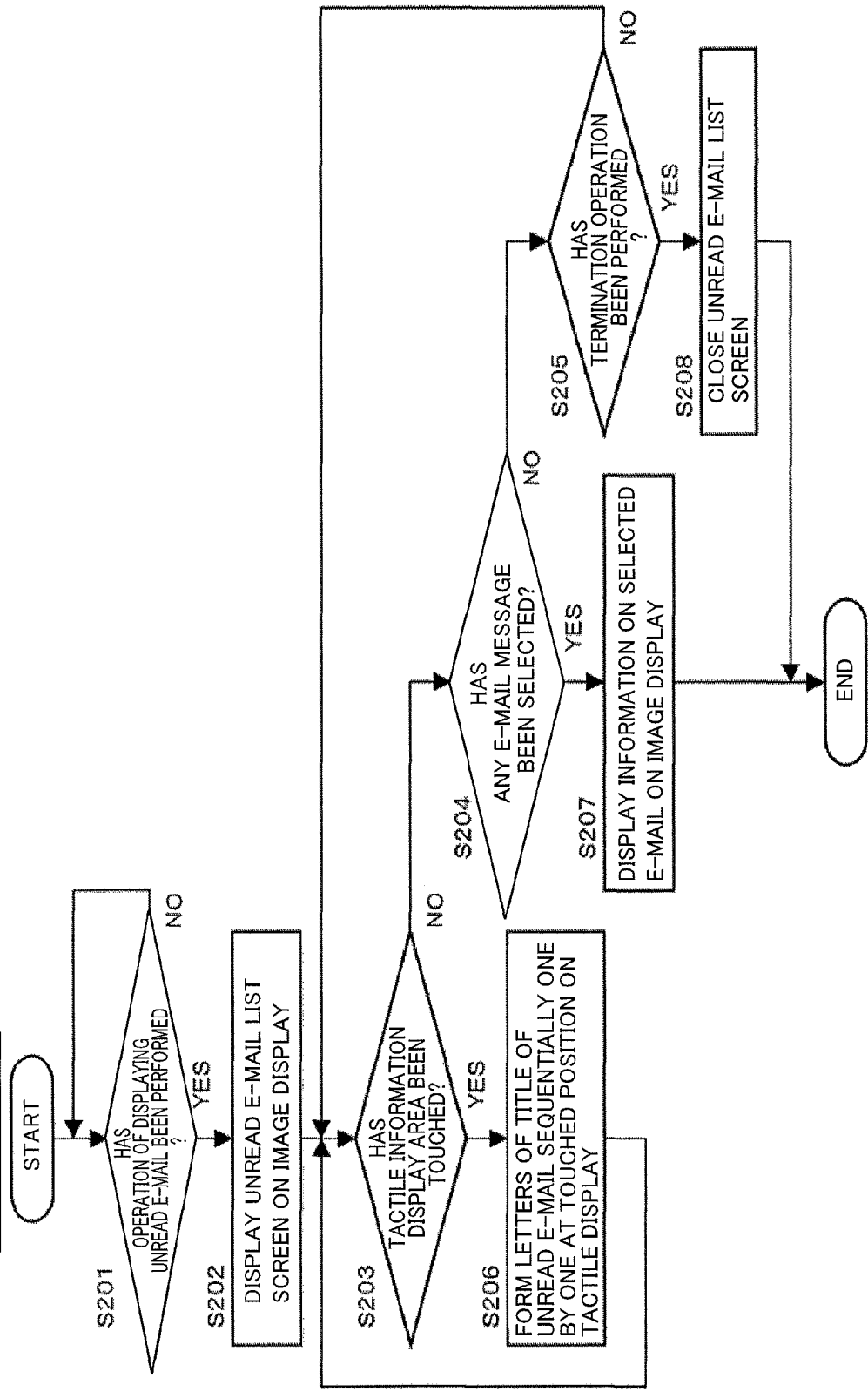
FIG. 9 is a flowchart showing a received e-mail display control process according to an embodiment.
Figure 11:
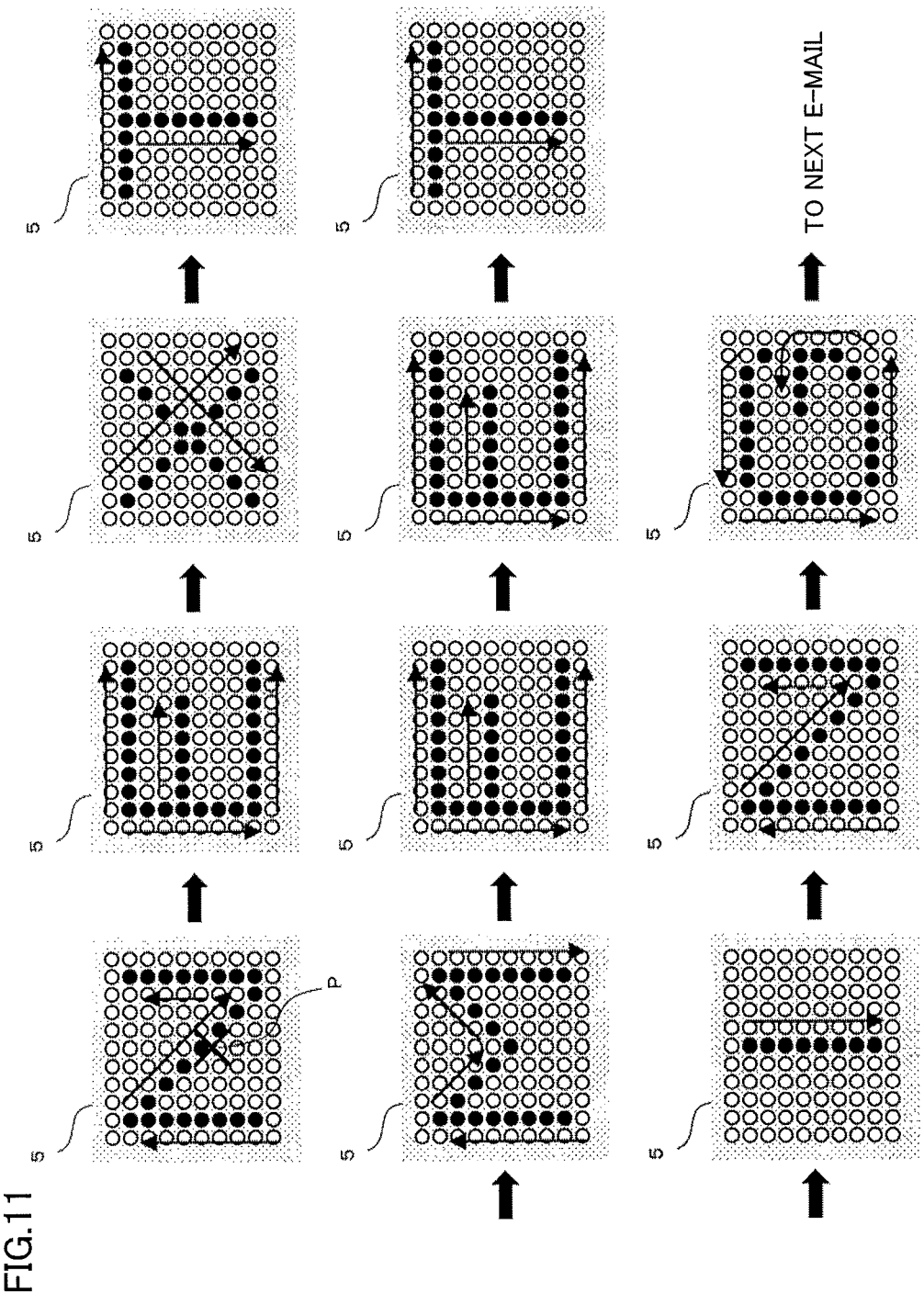
FIG. 11 is an explanatory drawing of an instance where the title of e-mail is displayed on the tactile display according to an embodiment.

FIG. 9 is a flowchart showing the received e-mail display control process. FIG. 10A shows image display 3 with an unread e-mail list screen 105 displayed thereon. FIG. 10B shows tactile display 5 with tactile information display area R set thereon. FIG. 11 shows how the title of e-mail is displayed on tactile display 5. FIGS. 10A, 10B and 11 show an instance where unread e-mail is titled "NEXT MEETING."

Referring to FIG. 9, controller 11 can determine whether or not a display operation for displaying unread e-mail has been performed (S201). Examples of the display operation include an operation on a specific hard key, a double-tap operation on image display 3, and the like.

A user can perform the display operation when he/she wants to check unread e-mail, such as when he/she becomes aware of receipt of new e-mail. If the display operation has been performed (YES in S201), controller 11 can cause image display 3 to display unread e-mail list screen 105 (S202). As shown in FIG. 10A, unread e-mail list screen 105 includes a list 105a in which unread e-mail messages are listed.

As shown in FIG. 10B, controller 11 can set tactile information display area R in a region on tactile display 5 avoiding notification bar 102, operation key group 103 and list 105a. Controller 11 can set a detection area corresponding to tactile information display area R on touch panel 4.

When unread e-mail list screen 105 is displayed, controller 11 can monitor whether or not tactile information display area R has been touched, whether or not any e-mail message has been selected in list 105a, and whether or not a termination operation has been performed (S203, S204, S205). The termination operation includes an operation on a specific hard key, a double-tap operation on image display 3, and the like.

For example, in a situation where a user cannot look at image display 3 but wants to know information on e-mail, he/she can touch tactile information display area R with his/her finger, as shown in FIG. 10B. Touch detection unit 14 can detect touched position P.

When tactile information display area R has been touched (YES in S203), controller 11 can form the letters representing the title of e-mail at touched position P sequentially one by one (S206), as shown in FIG. 11. On this occasion, controller 11 can perform the protrusion control operation and the trace control operation described with reference to FIGS. 6A to 6C sequentially on each letter. The trace control operation may be performed repeatedly twice or more. A time period during which no letter is formed exists between the letters.

Figure 12B:
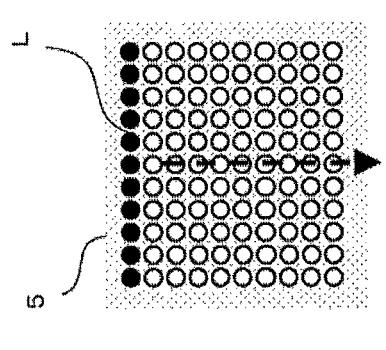
FIGS. 12A to 12C are explanatory drawings of an instance where the title of e-mail is displayed on the tactile display according to an embodiment.
Figure 12C:
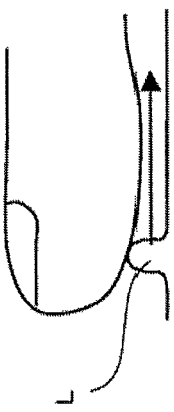
Figure 12A:
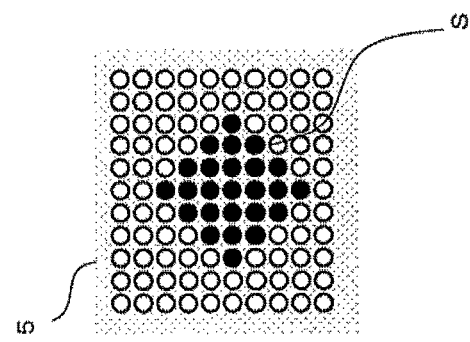

If there are several unread e-mail messages, the titles of the e-mail messages can be displayed on tactile display 5 one by one in reverse chronological order of received date, for example. After the display of one title finishes, controller 11 can perform a pause control operation of informing a user of a pause before transitioning to the display of the next title. For example, as shown in FIG. 12A, controller 11 can control tactile information output unit 15 such that a predetermined symbol S for indicating a pause is formed on tactile display 5 following the last letter of the title. Alternatively, controller 11 can control tactile information output unit 15 such that a laterally extending line L is moved downward subsequent to the last letter of the title, as shown in FIGS. 12B and 12C.

After terminating the operation in step S206, controller 11 can return the process to step S203, and can monitor again whether or not tactile information display area R has been touched.

When a user can look at image display 3 to check information on unread e-mail, he/she can perform a predetermined selection operation, for example, a tap operation, to select any e-mail message in list 105a. When any e-mail message has been selected (YES in S204), controller 11 can cause image display 3 to display information on the selected e-mail message, such as the title, sender's name and text (S207), and can terminate the received e-mail display control process.

When the check on unread e-mail is to be terminated, a user can perform a predetermined termination operation, for example, a double-tap operation. When the termination operation has been performed (YES in S205), controller 11 can close unread e-mail list screen 105 (S208) to terminate the received e-mail display control process.

The received e-mail display control process shown in FIG. 9 may always be executed as the control process for displaying unread e-mail. Alternatively, setting of a tactile display mode for executing the received e-mail display control process shown in FIG. 9 may be selectively made by a user. In addition to or instead of the title of e-mail, other pieces of information on the e-mail, such as the sender's name (sender information), text (as a whole or in part) and the like may be displayed on tactile display 5. A dedicated header field may be added to e-mail, and information included in the header field may be displayed on tactile display 5.

As described above, according to an embodiment, the trace control operation in which, when tactilely transferring text information to a user via tactile information output unit 15, electrical stimulation produced by respective electrode units 52 constituting letters varies in a predetermined order is executed. Since the user can feel a touch as if the shape of the letters is traced with his/her finger, it is easier for the user to recognize the letters.

According to an embodiment, since letters are formed at position P on tactile display 5 touched with a finger, a user does not need to search for the letters formed on tactile display 5 with his/her finger. Since letters are formed one by one at position P touched with his/her finger, the user does not need to move his/her finger for each letter. This is convenient for a user.

According to an embodiment, when there is an incoming call, a user can become aware of a caller of the incoming call by touching tactile display 5 with his/her finger even in a situation where he/she cannot look at image display 3.

According to an embodiment, when there is an incoming e-mail, a user can become aware of information on unread e-mail by touching tactile display 5 with his/her finger even in a situation where he/she cannot look at image display 3.

Although an embodiment has been described above, various variations can be made in addition to the foregoing.

<Variation 1>

In the above-described embodiment, a user can become aware of a caller via tactile display 5 while receiving an incoming call. In such a situation where a user cannot look at image display 3 and must check a caller tactilely, the user often cannot answer a call.

Mobile phone 1 of Variation 1 has a function of transmitting a message to a caller when a user cannot answer a call. Further, mobile phone 1 of Variation 1 may have a function of transmitting a message in accordance with the caller, if a user could have checked the caller.

FIG. 13A shows a structure of a message list 12c according to Variation 1. Memory 12 has message list 12c therein. Message list 12c can have a plurality of messages stored therein in association with transmission operations for transmitting the respective messages, respectively.

FIG. 13B is a flowchart showing a phone call control process according to Variation 1. FIG. 13B only shows the operations in steps S121 and S122 added to the phone call control process shown in FIG. 7 for the sake of convenience, and a description of the remaining operations is omitted.

When incoming call screen 104 is displayed, controller 11 can monitor whether or not a message transmission operation has been performed, in addition to monitoring whether or not tactile information display area R has been touched, whether or not response button 104a has been operated, and whether or not stop button 104b has been operated (S121). The transmission operation is a specific touch operation on image display 3, for example, a flick operation in a predetermined direction, such that a user can easily perform an operation even gropingly. When a flick operation is set as the transmission operation, a predetermined message is associated with a flick operation in each of the up/down and left/right directions, in message list 12c.

When a user checks a caller if he/she cannot answer a call, he/she can perform a transmission operation corresponding to a message to be transmitted to the caller. When any transmission operation has been performed (YES in S121), controller 11 can read a message corresponding to the performed transmission operation from message list 12c, and can transmit the message to a caller's phone via communication unit 20 (S122). For example, if the user has no intention of calling back a caller, a message saying that "I cannot answer a call now" can be transmitted, and if the user has an intention of calling back the caller, a message saying that "I'll call you back later" can be transmitted.

According to Variation 1, after checking a caller of an incoming call via tactile display 5, a user can send to the caller a message in accordance with the caller.

<Variation 2>

In the above-described embodiment, information on all of unread e-mail messages is displayed on tactile display 5 by the received e-mail display control process. In Variation 2, among unread e-mail messages, information on an urgent e-mail message (hereinafter, referred to as "urgent e-mail") that it is assumed that a sender wants to contact a user immediately is displayed on tactile display 5.

Memory 12 can have an urgent e-mail list 12*d* shown in FIG. 14A. Controller 11 can execute an urgent e-mail registration control process, and when it is determined that received e-mail is urgent e-mail, can register the e-mail in urgent e-mail list 12*d*.

FIG. 14B is a flowchart showing an urgent e-mail registration control process according to Variation 2.

When e-mail has been received (YES in S301), controller 11 can determine whether or not text of the received e-mail includes letters relevant to identification information (S302). The identification information includes letters indicating that an immediate contact is required, such as "urgent", "emergent" and "immediate", for example. When a sender wants to contact a user immediately, the sender adds letters indicating the identification information in the text of e-mail. If the text includes letters relevant to the identification information (YES in S302), controller 11 can register the received e-mail in urgent e-mail list 12*d* (S303).

FIG. 14C is a flowchart showing a received e-mail display control process according to Variation 2. FIG. 14C illustrates some operations including step S221 added to the received e-mail display control process shown in FIG. 9 for the sake of convenience, and a description of the remaining operations is omitted.

In Variation 2, if tactile information display area R has been touched (YES in S203), controller 11 can form letters representing the title of unread e-mail registered in urgent e-mail list 12*d* sequentially one by one at touched position P (S221).

According to Variation 2, among unread e-mail messages, a user can check information on a highly urgent e-mail message via tactile display 5. The user can send return e-mail to a sender immediately.

<Other Variations>

In the above-described embodiment, tactile display 5 forms letters by electrical stimulation from electrode units 52 located in a matrix. Tactile display 5 is not limited to the configuration of forming letters by electrical stimulation. For example, tactile display 5 may be configured to form letters by vibration stimulation which is one of tactile stimulation. In this case, transparent piezoelectric elements having a similar shape to electrode units 52 are located on tactile display 5 in a matrix, instead of electrode units 52. In this case, piezoelectric elements selected to foam letters are vibrated to transfer the shape of the letters to a user's finger. Since vibration stimulation produced by the respective piezoelectric elements varies so as to increase in a predetermined order, a user feels a touch as if the shape of the letters is traced with the surface of his/her finger.

In the above-described embodiment, tactile display 5 of substantially the same size as image display 3 is overlaid on image display 3. Tactile display 5 of a size smaller than image display 3 may be overlaid on image display 3. Tactile display 5 may be located on a portion of cabinet 2 which is different from image display 3, for example, on the rear surface of cabinet 2, rather than being overlaid on image display 3. In this case, the size of tactile display 5 may be the same as that of image display 3 or may be larger or smaller than image display 3. Tactile display 5 does not need to be transparent when it is not overlaid on image display 3.

In the above-described embodiment, tactile information display area R is set in tactile display 5. Tactile information display area R does not necessarily need to be set. For example, when a misoperation is unlikely to occur even when a touch is made at any position of tactile display 5, such as when an object, such as response button 104*a*, that would serve as an operation target is not displayed on image display 3, tactile information display area R does not need to be set.

In the above-described embodiment, the letters representing the caller's name or the title of e-mail are formed one by one at position P on tactile display 5 touched with a finger. The display of letters on tactile display 5 may be of any style. For example, letters may be formed one by one at a predetermined position on tactile display 5. In this case, it is desirable that when an initial letter is touched with a finger, the next letter be formed subsequent to the initial letter. A plurality of letters may be formed on tactile display 5 at once.

Figure 15:
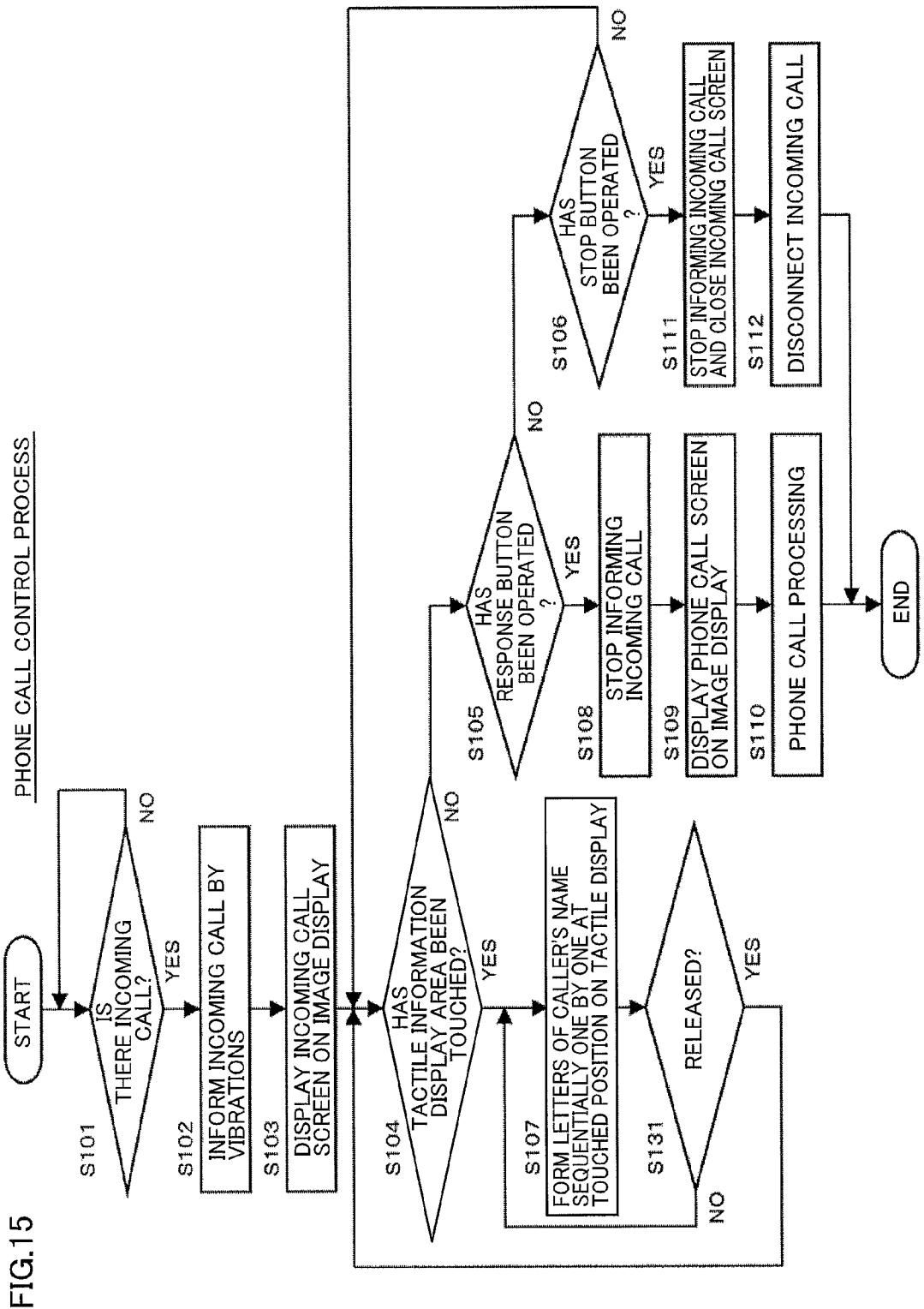
FIG. 15 is a flowchart showing a phone call control process according to another variation.

In the above-described embodiment, the caller's name is displayed only once on tactile display 5 while tactile information display area R is being touched with a finger. The caller's name may be displayed on tactile display 5 repeatedly while tactile information display area R is being touched with a finger. The trace control operation performed in step S107 shown in FIG. 7 may be performed repeatedly twice or more until a finger is released from tactile information display area R. The phone call control process in this case will be as shown in FIG. 15, and it is determined in step S131 whether or not the release has been performed subsequent to the operation in step S107. In this case, the upper limit number of times that the name is displayed while tactile information display area R is being touched may be set.

If the trace control operation is performed repeatedly twice or more, a time period during which no letter is formed may exist before the initial letter is formed since the last letter of the caller's name is formed. In that case, the time period during which no letter is formed may be longer than the time period during which no letter is formed between the letters of the caller's name.

Similarly, if tactile information display area R is being continuously touched when the titles of all unread e-mail messages are displayed, the display of the titles may be repeated twice or more from the initial unread e-mail message.

According to the above-described embodiment, caller information on an incoming call and information on unread e-mail (title information, sender information, text information, etc.) are displayed on tactile display 5. Information displayed on tactile display 5 is not limited to these types of information. For example, caller information on a missed call or information on a schedule created by the schedule function (title information, scheduled date information, etc.) may be displayed on tactile display 5. For example, when there is a missed call, a user is informed of the missed call by light emission of an LED (Light Emitting Diode) lamp, vibrations or the like. The user can become aware of the caller information on the missed call by touching tactile display 5. For example, in the case where a function in which information on a schedule is displayed on image display 3 when a time set by a user arrives has been set, when tactile information display area R is touched with the information on the schedule being displayed on image display 3, letters indicating the information on the schedule may be formed at the touched position.

The type of information displayed by tactile display 5 may be varied based on settings made by a user.

If a user is in a situation where he/she cannot check information on e-mail on image display 3, it is supposed that the user sets an automatic reply function to send back a fixed e-mail message automatically. Even in such a case where the automatic reply function has been set, the automatic reply function may be canceled temporarily when the tactile display mode for executing the received e-mail display control process is set. When the tactile display mode is set, it becomes possible for a user to check information on e-mail even in a situation where it is difficult for the user to check the information on image display 3. If a fixed e-mail message is no longer replied by canceling the automatic reply function, a sender will not assume with resignation that it is difficult for a user to reply. Thus, e-mail replied by the user is less likely to be neglected by the sender. Similarly, even if a guidance transmission function of transmitting an audio guidance to a missed call has been set, the guidance transmission function may be canceled temporarily when the manner mode is set and the phone call control process shown in FIG. 7 is executed.

In the above-described embodiment, the present disclosure is applied to a smartphone type mobile phone. The present disclosure is not limited thereto, but may be applied to other types of mobile phones, such as a bar phone, a flip phone, a slide phone, and the like.

An embodiment is not limited to mobile phones, but may be applied to various types of mobile terminal devices, such as a PDA (Personal Digital Assistant) and a tablet PC. An embodiment may be applied to a personal computer. In addition, an embodiment is applicable to various information transmission devices that transmit various types of information to a user.

In addition, various modifications can be made to an embodiment as appropriate within the scope of a technical idea recited in the claims.

(Other Aspects)

In an information transmission device according to an aspect, the stimulation applying units may each include an electrode unit which produces electrical stimulation. In this case, the at least one processor controls the information transmission unit such that a pressure sensed by a part of the human body having touched the electrode unit varies as the electrical stimulation produced by the electrode unit varies.

The information transmission device according to an aspect may be configured to further include a position detection unit which detects a position specified by a user in an area where the stimulation applying units are located. In this case, the at least one processor controls the information transmission unit such that a letter is formed at a position detected by the position detection unit.

With the above configuration, when transmitting a word or a phrase composed of a plurality of letters, the at least one processor may be configured to control the information transmission unit such that the letters are formed sequentially one by one at the position detected by the position detection unit.

The information transmission device according to an aspect may be configured to further include a communication unit which transmits/receives voice related to a call, a voice output unit which outputs the voice received by the communication unit, a voice input unit which inputs voice, and a first memory which stores caller information corresponding to a telephone number received by the communication unit. In this case, the at least one processor controls the communication unit, the voice input unit and the voice output unit to execute a telephone function. The at least one processor controls the information transmission unit such that letters representing the caller information are formed when there is an incoming call.

With the above configuration, the information transmission device may be configured to further include a second memory which stores a plurality of messages to be transmitted to a source device of the call. In this case, when an operation of selecting any of the messages for transmission is performed while receiving an incoming call, the at least one processor transmits the selected message from the communication unit to the source device of the call.

The information transmission device according to an aspect may be configured to further include a display and a communication unit which receives e-mail. In this case, the at least one processor causes the display to display information on the e-mail received by the communication unit. The at least one processor controls the information transmission unit such that a letter representing information on unread e-mail is formed.

With the above-described configuration, the at least one processor may be configured to control the information transmission unit such that a letter representing information on the unread e-mail extracted based on identification information included in the unread e-mail is formed.

A second aspect relates to an information transmission method through use of an information transmission unit including a plurality of stimulation applying units configured to apply tactile stimulation to a touched part of a human body. The information transmission method of an aspect includes selecting stimulation applying units for forming a letter from among the plurality of stimulation applying units each producing tactile stimulation, controlling each of the stimulation applying units selected for forming a letter to produce tactile stimulation, and varying the tactile stimulation produced by each of the selected stimulation applying units in a predetermined order.

Although the present disclosure has been described and illustrated in detail, it is clearly understood that the same is by way of illustration and example only and is not to be taken by way of limitation, the scope of the present disclosure being interpreted by the terms of the appended claims.

The invention claimed is:

1. An information transmission device comprising:
   an information transmission unit configured to tactilely transmit information;
   at least one processor configured to control the information transmission unit,
   the information transmission unit including a plurality of electrode units each configured to provide electrical stimulation to a portion of a user's body in contact with the plurality of electrode units, the at least one processor being configured to control the information transmission unit so as to cause the plurality of electrode units to be activated in a predetermined order to provide the electrical stimulation; and
   a touch panel configured to detect a touch in an area where the plurality of electrode units are located, wherein the plurality of electrode units are transparent and overlay the touch panel, and wherein the at least one processor is configured to control the information transmission unit such that a letter is traced by the activation of the plurality of electrode units in the predetermined order.

2. The information transmission device according to claim 1, wherein
the at least one processor is configured to control the information transmission unit such that a pressure sensed by a part of the human body having touched the electrode unit varies as the electrical stimulation produced by the electrode unit varies.

3. The information transmission device according to claim 1, wherein when transmitting a word or a phrase including a plurality of letters, the at least one processor is configured to control the information transmission unit such that the letters are formed sequentially one by one at the position detected by the position detection unit.

4. The information transmission device according to claim 1, further comprising:
a communication unit configured to transmit/receive voice related to a call;
a voice output unit configured to output the voice received by the communication unit;
a voice input unit configured to input voice; and
a first memory configured to store caller information corresponding to a telephone number received by the communication unit, wherein
the at least one processor is configured to
control the communication unit, the voice input unit and the voice output unit to execute a telephone function, and
control the information transmission unit such that a letter representing the caller information is formed when there is an incoming call.

5. The information transmission device according to claim 4, further comprising a second memory configured to store a plurality of messages to be transmitted to a source device of the call, wherein
the at least one processor is configured to, when an operation of selecting any of the messages for transmission is performed while receiving an incoming call, transmit the selected message from the communication unit to the source device of the call.

6. The information transmission device according to claim 1, further comprising:
a display; and
a communication unit configured to receive e-mail, wherein
the at least one processor is configured to
cause the display to display information on the e-mail received by the communication unit, and
control the information transmission unit such that a letter representing information on unread e-mail is formed.

7. The information transmission device according to claim 6, wherein the at least one processor is configured to control the information transmission unit such that a letter representing information on the unread e-mail extracted based on identification information included in the unread e-mail is formed.

8. An information transmission method through use of an information transmission unit including a plurality of electrode units configured to provide electrical stimulation to a portion of a user's body in contact with the plurality of electrode units, the information transmission method comprising:
selecting electrode units from the plurality of electrode units to provide the electrical stimulation; and
controlling each of the selected electrode units so as to cause the selected electrode units to be activated in a predetermined order so as to provide the electrical stimulation in a predetermined manner;
detecting a touch in an area of a touch panel where the plurality of electrode units are located, wherein the plurality of electrode units are transparent and overlay the touch panel; and
controlling the plurality of electrode units such that a letter is traced by the activation of the plurality of electrode units in the predetermined order.

* * * * *